United States Patent [19]

LeVahn

[11] Patent Number: 4,991,593

[45] Date of Patent: Feb. 12, 1991

[54] FLEXIBLE BAG FOR STORING BODY ORGANS

[75] Inventor: Bruce A. LeVahn, New Brighton, Minn.

[73] Assignee: Minnesota Scientific, Inc., Minneapolis, Minn.

[21] Appl. No.: 365,754

[22] Filed: Jun. 13, 1989

[51] Int. Cl.⁵ ............................................. A61F 13/00
[52] U.S. Cl. ................................... 128/856; 128/157; 128/853; 128/DIG. 24
[58] Field of Search ............... 128/849, 850, 851, 853, 128/856, 82, 155, 157, 918, DIG. 24; 383/71-75, 46, 90-92

[56] References Cited

U.S. PATENT DOCUMENTS

| | | | |
|---|---|---|---|
| 1,084,228 | 1/1914 | Quisenberry et al. | 383/41 |
| 1,748,087 | 2/1930 | Spanel | 15/257 R |
| 2,444,996 | 7/1948 | Lebenhart | 383/92 X |
| 2,497,325 | 2/1950 | Scherba | 150/52 |
| 2,528,562 | 11/1950 | Swanson | 383/92 X |
| 2,835,253 | 5/1958 | Borgeson | 128/850 X |
| 3,111,943 | 11/1963 | Orndorff | 128/850 |
| 3,150,640 | 9/1964 | Nevitt | 119/96 |
| 3,221,742 | 12/1965 | Orowan | 128/283 |
| 3,244,169 | 4/1966 | Baxter | 128/82 |
| 3,435,821 | 4/1969 | Bennett | 128/850 X |
| 3,863,639 | 2/1975 | Kleaveland | 128/850 |
| 3,920,179 | 11/1975 | Hall | 383/72 X |
| 4,024,872 | 5/1977 | MacDoon | 128/850 X |
| 4,328,605 | 5/1982 | Hutchison et al. | 24/115 G |
| 4,453,292 | 6/1984 | Bakker | 24/115 G |
| 4,675,948 | 6/1987 | Bengtsson | 24/115 G |
| 4,777,943 | 10/1988 | Chuadil | 128/853 X |

FOREIGN PATENT DOCUMENTS 507365 9/1920 France ..................................... 383/93

Primary Examiner—Robert A. Hafer
Assistant Examiner—Kevin G. Rooney
Attorney, Agent, or Firm—Kinney & Lange

[57] ABSTRACT

A device for maintaining a body organ during surgery includes a flexible enclosure having at least one opening large enough to permit the body organ to pass through and including means for limiting closure of the opening such that injury to the body organ is minimized.

11 Claims, 3 Drawing Sheets

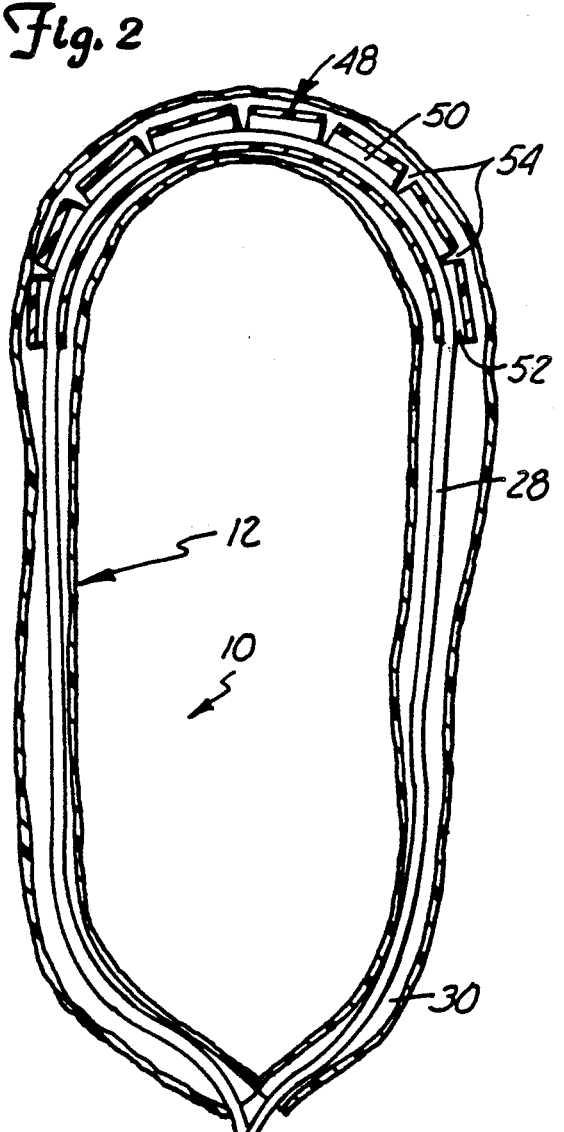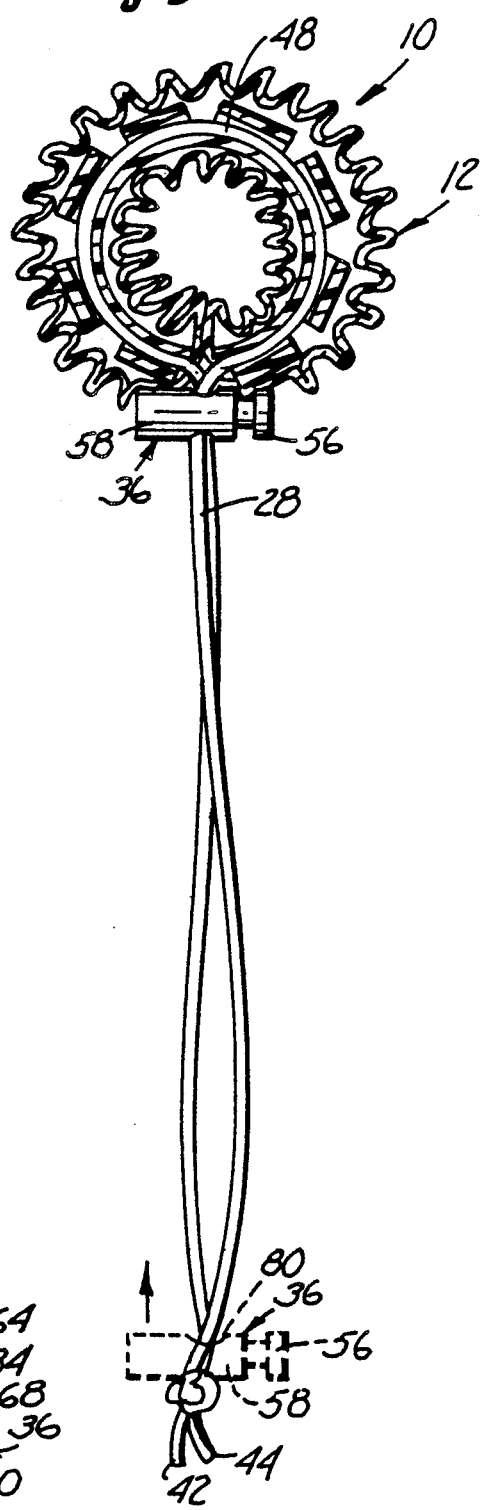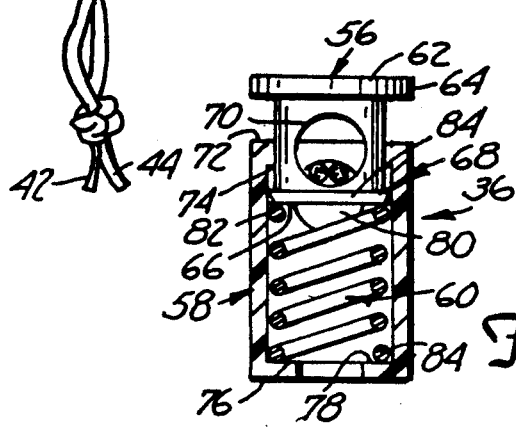

FLEXIBLE BAG FOR STORING BODY ORGANS

BACKGROUND OF THE INVENTION

1. Field of the Invention.

The present invention relates to surgical devices. In particular, the present invention relates to a flexible bag for temporarily storing body organs during surgery.

2. Description of the Prior Art.

It is often necessary during surgery to temporarily remove organs from the body cavity. Certain organs, especially the bowels, have a tendency to dry during surgery and are subject to injury during handling.

It is sometimes necessary during surgery to lift body organs out of the abdominal cavity. The surgeon may repair the organ outside the body cavity or may need to set aside an organ in order to create enough space to operate on other organs in the body cavity.

The Baxter U.S. Pat. No. 3,244,169 describes a flexible bag for use when surgery requires that the organ be temporarily placed outside the body cavity. The flexible bag has two opposing ends, the first end having a drawstring closure device for closing the bag after an organ is placed in it, and the second end having an opening with a smaller diameter than the diameter of the first end. The surgeon passes his hand through the first end, and then through the second end. The surgeon then slides the second end over the organ to be protected. The first end is sealed by pulling the drawstring. The second end fits loosely over the organ that is to be protected.

The Scherba U.S. Pat. No. 2,497,325 describes a bag used for storing shoes, and has two open ends that are each closed by a drawstring. Similarly, the Spanel U.S. Pat. No. 1,748,087 shows a bag for use as a renovating device with two opposite ends, each with a drawstring.

The Nevitt U.S. Pat. No. 3,150,640 shows a restraint bag for animals. The bag has one open end that closes around the neck of an animal. The bag is tapered at the open end, and the material of construction is flexible and impermeable to liquids.

The Quisenberry et al U.S. Pat. No. 1,084,228 shows a bag having two open ends for use in carrying cotton. The Orowan U.S. Pat. No. 3,221,742 discloses a receptacle for collecting human bodily waste. It has two ends, the first end equipped with a disk-shaped object having a hole in the middle fixing the size of the first end.

SUMMARY OF THE INVENTION

The present invention includes a device for maintaining a body organ during surgery. The device includes a flexible enclosure having at least one opening large enough to permit the body organ to pass through, and means for limiting the closure of the opening such that when the opening is closed, injury to the body organ is prevented.

BRIEF DESCRIPTION OF THE DRAWINGS

FIG. 2 is a cross-sectional view of a preferred embodiment of the present invention with the first end in the open position.

FIG. 3 is a cross-sectional view of a preferred embodiment of the present invention with the first end in the closed position.

FIG. 4 is a cross-sectional view of a spring-loaded lock of the present invention.

DETAILED DESCRIPTION OF THE PREFERRED EMBODIMENTS

Figure 1:
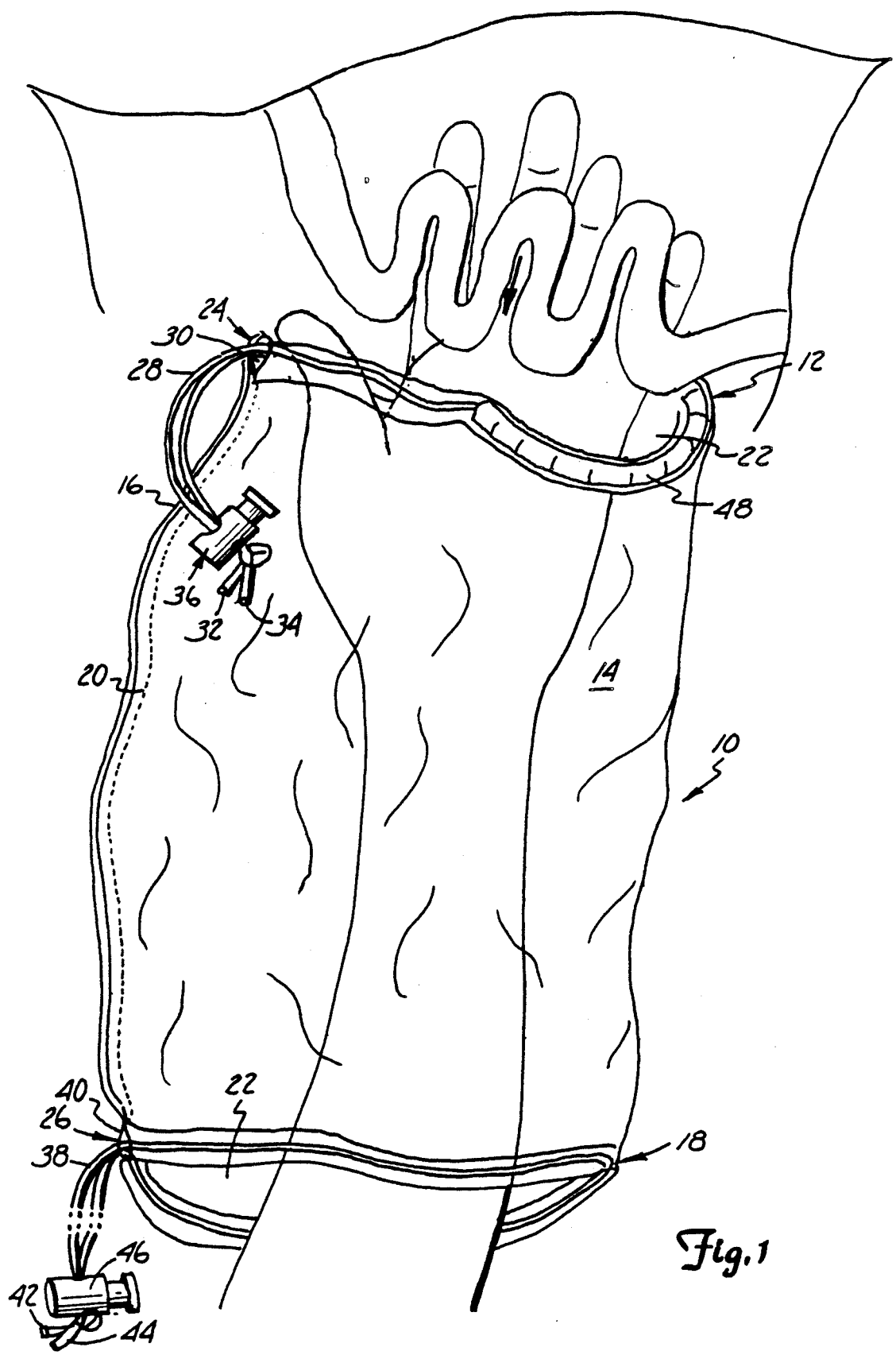
FIG. 1 is a perspective view of a preferred embodiment of the present invention.

A flexible bag of the present invention is generally illustrated at 10 in FIG. 1. The preferred embodiment of the flexible bag has a first end 12 and a main body portion 14 of a substantially tubular shape having a tapered section 16. The flexible bag 10 has a second end 18 that is located opposite the first end 12 of the main body portion 14.

The main body portion 14 in the preferred embodiment is constructed of a sheet of flexible plastic material. The sheet is folded in half and sealed along a seam 20 extending from the first end 12 to the second end 18. The tapered section 16 in the preferred embodiment is located along the seam 20 and tapers inwardly from a point approximately six inches from the first end 12 inwardly terminating at the first end 12. In the preferred embodiment, the first end 12 is of a smaller diameter than the second end 18.

The main body portion 14 defines a cavity 22 which extends from the first end 12 to the second end 18. The surgeon positions the flexible bag 10 of the present invention on the outside of a body organ by placing his hand into the second end 18, through the cavity 22, and out through the first end 12. With the flexible bag 10 positioned on the lower arm, the surgeon lifts a body organ out of the body cavity and slides the first end 12 of the flexible bag 10 over the body organ.

In the preferred embodiment, the main body portion 14 is sized to receive a portion of a human intestine. The flexible bag 10 in the preferred embodiment measures about twelve inches from the first end 12 to the second end 18. The first end 12 is about fourteen inches in circumference and the second end 18 is about eighteen inches in circumference. In the preferred embodiment, the main body portion 14 has a seam 20 located inwardly on the main body portion 14.

The main body portion 14 of the preferred embodiment is constructed of 0.004 inch thick translucent polypropylene plastic. The plastic is transparent in order for the surgeon to monitor the condition of the body organ during surgery. In another embodiment, the main body portion 14 is opaque.

Body organs that are not adequately protected during extensive surgery are susceptible to damage due to loss of moisture. The main body portion 14 of the present invention is constructed of a material that is substantially impermeable to water vapor. The use of a flexible bag 10 that is substantially impermeable to water vapor has certain advantages. In particular, it eliminates the necessity to irrigate the body organ regularly during surgery. Irrigation of the organ can increase the potential for infection, and the risk of potential tissue damage. Any main body portion 14 formed of a material that is relatively impermeable to liquids and that is flexible and capable of a variety of sterilization methods such as radiation sterilization, or ethylene oxide gas sterilization, for example is suitable to form a flexible bag 10 of the present invention.

The first end 12 has a first closure device 24 and the second end 18 has a second closure device 26. In one preferred embodiment, the first closure device 24 includes a first drawstring 28 and a first sleeve 30. The first sleeve 30 is formed by folding the first end 12 inwardly toward the cavity 22 and sealing the end onto the main body portion 14 at a point about three fourths of an inch from the first end 12. The sleeve is sealed by conventional means such as a heat seal. The first drawstring 28 is positioned in the passage defined by the sleeve 30.

The first drawstring 28 has a first end 32 and a second end 34. In the preferred embodiment, the first end 32 and the second end 34 of the drawstring 28 are joined together with a first spring-loaded lock 36.

The second closure device 26 is located on the second end 18 of the main body portion 14. The second closure device 26 includes a second drawstring 38 and a second sleeve 40. The second sleeve 40 is integrally formed with the main body portion 14 by folding the second end 18 of the main body portion 14 inwardly from the first end 18 and sealing the first end 18 onto the main body portion 14 at a point about three quarters of an inch from the first end 18. The second sleeve 40 is sealed by conventional means such as heat sealing. The second drawstring 38 is positioned in a passage defined by the second sleeve 40. The second drawstring 38 has a first end 42 and a second end 44. In the preferred embodiment, the first end 42 and the second end 44 are held together by a second spring-loaded lock 46.

In the preferred embodiment, the first and second drawstrings 28 and 38 are constructed of braided nylon cord. The present invention contemplates the use of other suitable materials such as polypropylene chord, for example. Any flexible chord capable of being sterilized by standard methods such as gamma radiation or ethylene oxide gas treatment, for example is suitable for use as drawstrings 28 and 38.

A cross sectional view of the first end 12 of the present invention is indicated at FIG. 2. The first sleeve 30 has a closure limiting device 48 for preventing the first end 12 from being tightened enough to injure a body organ contained in the flexible bag 10. The closure limiting device 48 in the preferred embodiment includes a section of plastic tubing 50 of about four inches in length. In the preferred embodiment, the tubing 50 is approximately one fourth inch outer diameter and is of semi-rigid construction.

The tubing 50 defines a tubing cavity 52 of a substantially cylindrical shape. The first drawstring 28 passes through the tubing cavity 52. In the preferred embodiment, a semi-rigid tubing 50 is used as a closure limiting device 48. In order for the tubing 50 of the preferred embodiment to bend to a small radius, a plurality of notches 54 are cut in the tubing 50.

In the preferred embodiment, the notches 54 extend radially, that is, substantially perpendicular to the original axis of the tubing 50. The rigidity of the material selected to form the tubing 50 determines the depth of the notches 54 and the quantity of the notches 54 necessary to achieve the required flexibility. In the preferred embodiment, the tubing 50 has a cross sectional area, and seven equally spaced notches 54, each bisecting about one half of the cross sectional area.

In the preferred embodiment, the tubing 50 has a wall thickness of approximately one sixteenth of an inch and is constructed of polyethylene. The present invention contemplates the use of tubing such as medical tubing sold by the Norton Company under the trademark "Tygon". Silicone, polyproplyene, and fluorocarbon tubing such as tubing sold by the E. I. Du Pont de Nemours Company under the trademark "Teflon" and others in a variety of wall thicknesses are also suitable types of tubing for use in the present invention. Any tubing that can be sterilized by standard methods such as gamma radiation, or ethylene oxide gas treatment, for example, would be suitable for this purpose.

Alternatively, other types of closure limiting means are included within the present invention. For example, beads or knots used to limit the amount that the draw string 28 can be pulled are also includable within the present invention.

A cross-sectional view of the first end 12 of the flexible bag 10 is indicated at FIG. 3. After the surgeon places the body organ in the flexible bag 10, he pulls the first drawstring 28 until the closure limiting device 48 bends into a substantially circular shape. Because the main body portion 14 (as shown in FIG. 1) of the flexible bag 10 has a tapered section 16, the diameter of the first end 12 is less than the diameter of the second end 18, reducing the quantity of material gathered at the first end 12.

A cross-sectional view of the first drawstring lock 36 indicated at FIG. 4 has three components. The drawstring lock 38 has a plunger 56, a barrel 58, and a spring 60. The plunger 56 has a first end 62 having a flange 64 projecting radially outward for use as an axial stop. The plunger 56 has a second end 66 having a tapered flange 68 projecting radially outward for limiting the total axial travel of the plunger 56. The plunger 56 has an outer cylindrical surface and two opposite circular holes 70 located on the outer cylindrical surface. In the preferred embodiment, the circular holes 70 are the same distance from the first end 62. In the preferred embodiment, the plunger 56 is constructed of a rigid plastic such as polyvinyl chloride.

The barrel 58 has an inner cylindrical surface and an outer cylindrical surface. The diameter of the inner cylindrical surface is slightly larger than the diameter of the tapered flange 68 of the second end 66 of the plunger 56. The barrel 58 has a first end 72 having an inner shoulder 74 and the second end 76 having an inner shoulder 78. The barrel 58 has two opposite circular holes 80 located on the outer cylindrical surface. The holes 80 are spaced an equal distance from the first end 72 of the barrel 58. The barrel 58 in the preferred embodiment is constructed of rigid plastic material such as polyvinyl chloride.

The inner shoulders 74 and 78 of the barrel 58 are axial stops. The first drawstring lock 36 has a compression spring 60 that is of helical shape and has an outer diameter approximately equal to the inner diameter of inner shoulder 74 of the barrel 58. The spring 60 is positioned in the annular space defined by the inner cylindrical surface of the barrel 58. The spring 60 in the preferred embodiment has a first end 82 and a second end 84. The first end 82 rests on the second end 66 of the plunger 56 and the second end 84 rests on the inner shoulder 78 of the barrel 58.

The second end 66 of the plunger 56 has a male tapered outer surface 84 and is positioned in the aperture defined by the inner cylindrical surface of the barrel 58. The inner shoulder 74 of the of the first end 72 of the barrel 58 is of a slightly smaller diameter than the largest portion of the outer tapered surface 84. By sliding the second end 66 of the plunger 56 past the inner shoulder 74, the plunger 56 is locked into sliding engagement with the barrel 58.

The spring 60 is positioned between the second end 66 of the plunger 56 and the inner shoulder 78 of the barrel 58, and forces the surfaces apart.

The first spring-loaded lock 36 (shown in FIG. 3) is positioned on the first drawstring 28 by rotating the plunger 56 in the barrel 58 until the pair of opposite holes 70 in the plunger 56 radially align with the pair of opposite holes 80 in the barrel 58. The spring 60 is compressed by exerting force on the first end 62 of the plunger 56 and exerting an opposite force on the second end 76 of the barrel 58.

The first end 42 and the second end 44 (as shown in FIG. 2) are passed through the first hole 80 of the barrel 58, the pair of holes 70 of the plunger 56, and then through the second hole 80 of the barrel 58. The spring-loaded lock 36 is positioned along the length of the first drawstring 28 by first exerting pressure on the first end 62 of the plunger 56 and oppositely on the second end 76 of the barrel 58. By compressing the spring, the holes 70 and 80 move into axial alignment, and the force is released from the drawstring 28. The first spring-loaded lock 36 is moved into the desired position, and then the pressure is released to force the holes 70 and 80 out of axial alignment, locking the drawstring into place. In the preferred embodiment, the spring 60 is of standard metal alloy construction.

Figure 5:
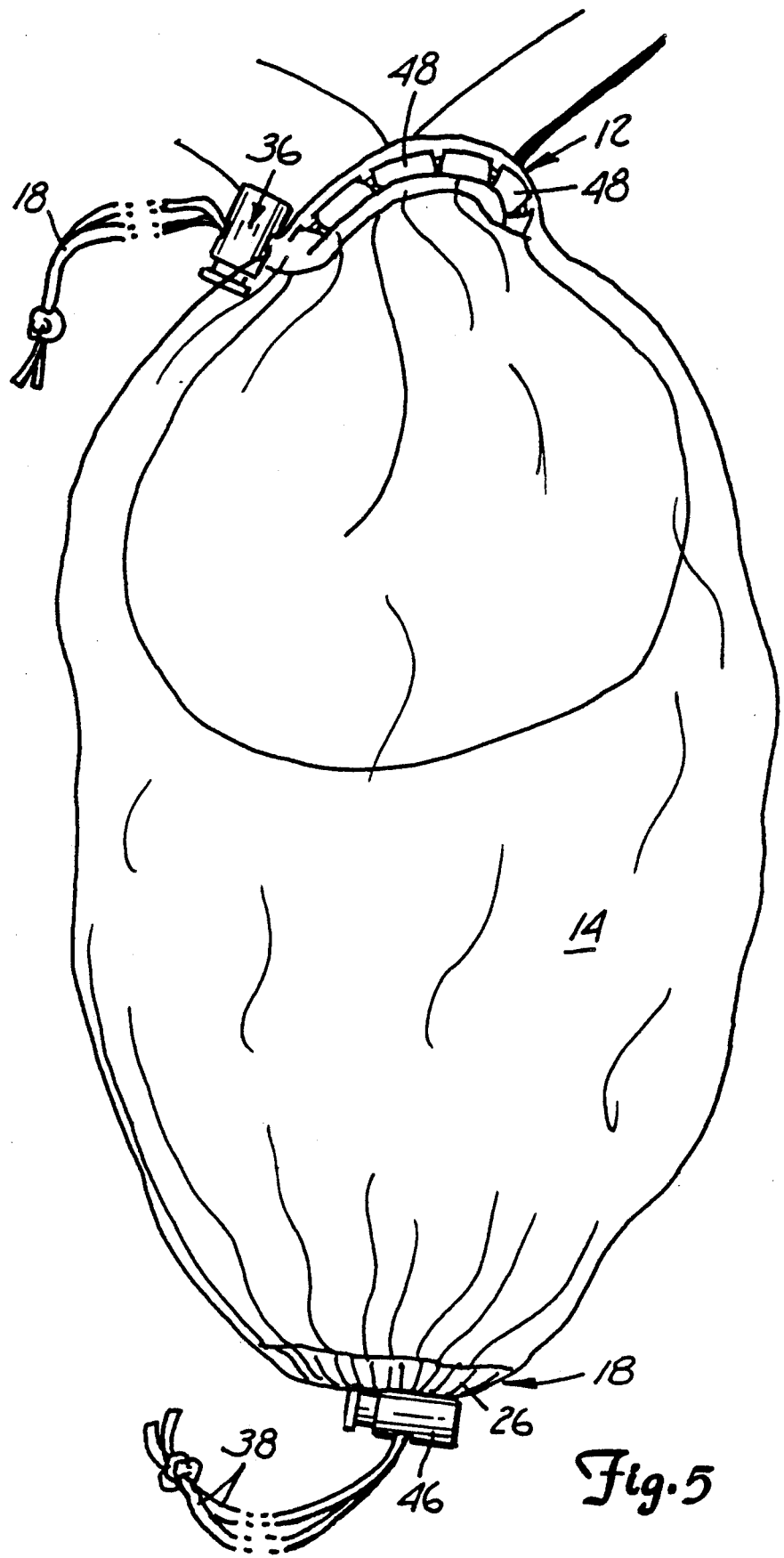
FIG. 5 is a perspective view of the device of the present invention with the closure devices drawn, and containing a section of a human intestine.

A perspective view of the preferred embodiment in use is illustrated in FIG. 5. The second end 18 of the main body portion 14 has a second closure device 26. In the preferred embodiment, the second closure device has a second drawstring 38 having a second spring-loaded lock 46 which is substantially identical to the first spring-loaded lock 36 described above.

The bag 10 contains a section of a human intestine. The first end 12 is closed against the intestinal wall, and the closure limiting device 48 protects the intestine from damage from over tightening. The second end 18 is closed to protect the intestine from microbial contamination and tissue damage resulting from drying and exposure.

Although the present invention has been described with reference to preferred embodiments, workers skilled in the art will recognize that changes may be made in form and detail without departing from the spirit and scope of the invention.

What is claimed is:

1. A device for maintaining a body organ during surgery, comprising:

a flexible enclosure having first and second openings, the first opening being large enough to permit the body organ to pass through;

means for closing the first opening of the flexible enclosure; and semi-rigid means for limiting closure of the first opening such that injury to the body organ is minimized, the semi-rigid means including sleeve means proximate the opening and forming a circumferential passage, drawstring means including at least one drawstring positioned in the circumferential passage and a flexible tube having a passage extending therethrough, the flexible tube being positioned in the circumferential passage, and at least one draw string being positioned in the passage of the tube.

2. The device of claim 1 wherein the flexible enclosure is transparent.

3. The device of claim 1 wherein the flexible enclosure is of plastic construction.

4. The device of claim 1 wherein the flexible enclosure is constructed of plastic having a thickness of about 0.002 to 0.008 inch.

5. The device of claim 1 wherein the flexible enclosure is opaque.

6. The device of claim 1 wherein the flexible enclosure has a substantially cylindrical portion.

7. The device of claim 1 wherein the flexible enclosure has a tapered portion tapering inwardly toward the first opening.

8. The device of claim 1 wherein the flexible enclosure is substantially impermeable to liquids.

9. The device of claim 1 and further including a drawstring lock in cooperative engagement with the drawstring.

10. The device of claim 9 wherein the drawstring lock comprises:

a compression spring;

a plunger portion having a first locking surface, an outer surface and a pair of oppositely spaced holes on the outer surface for encircling the drawstring; and a barrel portion having an outer surface, a pair of oppositely spaced holes on the outer surface for encircling the drawstring, an aperture for receiving the first locking surface, and an inner annular space for containing the compression spring.

11. The device of claim 1 wherein the flexible tube has a tube wall and a plurality of notches cut through a portion of the tube wall sufficiently deep to provide sufficient flexibility such that the tubing bends and still provides protection to the body organ.

* * * * *